United States Patent [19]

Porro

[11] Patent Number: 5,652,211
[45] Date of Patent: *Jul. 29, 1997

[54] PEPTIDES FOR NEUTRALIZING THE TOXICITY OF LIPID A

[75] Inventor: Massimo Porro, Siena, Italy

[73] Assignee: BiosYnth S.r.l., Siena, Italy

[*] Notice: The term of this patent shall not extend beyond the expiration date of Pat. No. 5,371,186.

[21] Appl. No.: 97,830

[22] Filed: Jul. 26, 1993

Related U.S. Application Data

[63] Continuation-in-part of Ser. No. 49,871, Apr. 19, 1993, Pat. No. 5,358,933, and Ser. No. 819,893, Jan. 16, 1992, Pat. No. 5,371,186, which is a continuation-in-part of Ser. No. 658,744, Feb. 11, 1991, abandoned, said Ser. No. 49,871, is a continuation of Ser. No. 658,744.

[51] Int. Cl.$^6$ .................. A61K 38/08; A61K 38/10; A61K 38/16; C07K 7/06
[52] U.S. Cl. .................. 514/11; 514/12; 514/14; 514/15; 514/16; 514/17; 530/324; 530/327; 530/328; 530/329; 530/350; 530/317
[58] Field of Search .................. 514/13–16, 11, 514/12, 17, 564; 530/317, 324, 326, 329, 350

[56] References Cited

U.S. PATENT DOCUMENTS

| | | | |
|---|---|---|---|
| 4,683,291 | 7/1987 | Zimmerman et al. | 530/324 |
| 5,194,586 | 3/1993 | Maeda et al. | 530/324 |
| 5,358,933 | 10/1994 | Porro | 514/15 |
| 5,371,186 | 12/1994 | Porro | 530/328 |

FOREIGN PATENT DOCUMENTS

| | | | |
|---|---|---|---|
| 0304279 | 2/1989 | European Pat. Off. | C07K 7/04 |
| 423649 | 4/1991 | European Pat. Off. | C07K 7/00 |
| 0943 | 11/1992 | South Africa . | |
| 8901486 | 2/1989 | WIPO | C07K 3/08 |

OTHER PUBLICATIONS

Peptides, vol. 14, issued 1993, Mohri et al, "Synthetic Peptides Inhibit The Interaction of von Willebrand . . . ", pp. 125–129.
Science, vol. 259, Jan. 1993, Alessandro Rustici et al., "Molecular Mapping and Detoxification of the Lipid A Binding Site by Synthetic Peptides", pp. 361–365.
Merrick et al, Biochimica et Biophysica Acta vol. 1050 pp. 235–240 (1990).
Weber et al, J. Biol. Chem. vol. 263 pp. 11421–11425 (1988).
Simmons et al, Blood vol. 73 pp. 284–289 (1989).
Blasi et al, Yeast vol. 9, pp. 21–32 (Jan. 1993).
Aketagawa et al. J. Biol. Chem. vol. 261 pp. 7357–7365 (1986).
Schumann et al. Science vol. 249 pp. 1429–1431 (1990).
Gray et al. J. Biol. Chem vol. 264 pp. 9505–9509 (1989).

*Primary Examiner*—Jeffrey E. Russell
*Attorney, Agent, or Firm*—Hedman, Gibson & Costigan, P.C.

[57] ABSTRACT

The present invention is concerned with a peptide composition which includes a peptide having units of the formula:

(a) $(A)_n$ wherein A is Lysine or Arginine and n is an integer with a minimum value of 7.

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which Is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2. The compositions of the invention bind Lipid-A of endotoxins.

39 Claims, No Drawings

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:1:

Lys  Lys  Lys  Lys  Lys  Lys  Lys  Lys  Lys  Lys
        1                5                      10

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) TOPOLOGY: linear ( i i ) SEQUENCE DESCRIPTION: SEQ ID NO:2:

```
        Lys Lys Lys Lys Lys Lys Lys Lys Lys Lys Lys Lys Lys Lys
          1               5                       10
        Lys Lys Lys Lys Lys Lys Lys Lys Lys Lys Lys Lys Lys Lys
         15                      20                      25
        Lys Lys
         30
```

(2) INFORMATION FOR SEQ ID NO:3:

(i) SEQUENCE CHARACTERISTICS:
        (A) LENGTH: 434 amino acids
        (B) TYPE: amino acid
        (C) TOPOLOGY: linear (ii) SEQUENCE DESCRIPTION: SEQ ID NO:3:

```
Lys Lys Lys Lys Lys Lys Lys Lys Lys Lys Lys Lys Lys Lys Lys
 1               5                      10                      15
Lys Lys Lys Lys Lys Lys Lys Lys Lys Lys Lys Lys Lys Lys Lys
                20                      25                      30
Lys Lys Lys Lys Lys Lys Lys Lys Lys Lys Lys Lys Lys Lys Lys
                35                      40                      45
Lys Lys Lys Lys Lys Lys Lys Lys Lys Lys Lys Lys Lys Lys Lys
                50                      55                      60
Lys Lys Lys Lys Lys Lys Lys Lys Lys Lys Lys Lys Lys Lys Lys
                65                      70                      75
Lys Lys Lys Lys Lys Lys Lys Lys Lys Lys Lys Lys Lys Lys Lys
                80                      85                      90
Lys Lys Lys Lys Lys Lys Lys Lys Lys Lys Lys Lys Lys Lys Lys
                95                     100                     105
Lys Lys Lys Lys Lys Lys Lys Lys Lys Lys Lys Lys Lys Lys Lys
               110                     115                     120
Lys Lys Lys Lys Lys Lys Lys Lys Lys Lys Lys Lys Lys Lys Lys
               125                     130                     135
    Lys Lys Lys Lys Lys Lys Lys Lys Lys Lys Lys Lys Lys Lys
               140                     145                     150
      Lys Lys Lys Lys Lys Lys Lys Lys Lys Lys Lys Lys Lys Lys
               155                     160                     170
      Lys Lys Lys Lys Lys Lys Lys Lys Lys Lys Lys Lys Lys Lys
               175                     180                     185
      Lys Lys Lys Lys Lys Lys Lys Lys Lys Lys Lys Lys Lys Lys
               190                     195                     200
      Lys Lys Lys Lys Lys Lys Lys Lys Lys Lys Lys Lys Lys Lys
               205                     210                     215
      Lys Lys Lys Lys Lys Lys Lys Lys Lys Lys Lys Lys Lys Lys
               220                     225                     230
      Lys Lys Lys Lys Lys Lys Lys Lys Lys Lys Lys Lys Lys Lys
               235                     240                     245
      Lys Lys Lys Lys Lys Lys Lys Lys Lys Lys Lys Lys Lys Lys
               250                     255                     260
      Lys Lys Lys Lys Lys Lys Lys Lys Lys Lys Lys Lys Lys Lys
               265                     270                     275
      Lys Lys Lys Lys Lys Lys Lys Lys Lys Lys Lys Lys Lys Lys
               280                     285                     290
      Lys Lys Lys Lys Lys Lys Lys Lys Lys Lys Lys Lys Lys Lys
               295                     300                     305
```

| | | | | Lys | | | | | Lys | | | | | Lys |
|---|---|---|---|---|---|---|---|---|---|---|---|---|---|---|
| Lys | Lys | Lys | Lys | Lys<br>310 | Lys | Lys | Lys | Lys | Lys<br>315 | Lys | Lys | Lys | Lys | Lys<br>320 |
| Lys | Lys | Lys | Lys | Lys<br>325 | Lys | Lys | Lys | Lys | Lys<br>330 | Lys | Lys | Lys | Lys | Lys<br>335 |
| Lys | Lys | Lys | Lys | Lys<br>335 | Lys | Lys | Lys | Lys | Lys<br>340 | Lys | Lys | Lys | Lys | Lys<br>345 |
| Lys | Lys | Lys | Lys | Lys<br>350 | Lys | Lys | Lys | Lys | Lys<br>355 | Lys | Lys | Lys | Lys | Lys<br>360 |
| Lys | Lys | Lys | Lys | Lys<br>365 | Lys | Lys | Lys | Lys | Lys<br>370 | Lys | Lys | Lys | Lys | Lys<br>375 |
| Lys | Lys | Lys | Lys | Lys<br>380 | Lys | Lys | Lys | Lys | Lys<br>385 | Lys | Lys | Lys | Lys | Lys<br>390 |
| Lys | Lys | Lys | Lys | Lys<br>395 | Lys | Lys | Lys | Lys | Lys<br>400 | Lys | Lys | Lys | Lys | Lys<br>405 |
| Lys | Lys | Lys | Lys | Lys<br>410 | Lys | Lys | Lys | Lys | Lys<br>415 | Lys | Lys | Lys | Lys | Lys<br>420 |
| Lys | Lys | Lys | Lys | Lys<br>425 | Lys | Lys | Lys | Lys | Lys<br>430 | Lys | Lys | Lys | Lys<br>434 | |

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:4:

Lys Glu Lys Glu Lys Glu Lys Glu Lys Glu
        1                 5                   10

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:5:

Lys Phe Lys Phe Lys Phe Lys Phe Lys Phe
        1                 5                   10

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) TOPOLOGY: linear ( i i ) SEQUENCE DESCRIPTION: SEQ ID NO:6:

Lys Phe Leu Lys Lys Thr Leu
        1                 5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) TOPOLOGY: linear ( i i ) SEQUENCE DESCRIPTION: SEQ ID NO:7:

Lys Phe Leu Lys Phe Leu Lys
        1                 5

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:8:

```
Lys  Phe  Leu  Lys  Phe  Leu  Lys  Phe  Leu  Lys
1                  5                          10
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) TOPOLOGY: linear ( i i ) SEQUENCE DESCRIPTION: SEQ ID NO:9:

```
Arg  Tyr  Val  Arg  Tyr  Val  Arg  Tyr  Val
1                  5
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:10:

```
Lys  Phe  Phe  Lys  Phe  Phe  Lys  Phe  Phe  Lys
1                  5                          10
```

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) TOPOLOGY: linear ( i i ) SEQUENCE DESCRIPTION: SEQ ID NO:11:

```
Lys  Leu  Leu  Lys  Leu  Leu  Lys  Leu  Leu
1                  5
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:12:

```
Lys  Lys  Lys  Lys  Lys  Lys  Phe  Lys  Phe  Lys
1                  5                          10
```

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) TOPOLOGY: circular ( i x ) FEATURE:
        ( D ) OTHER INFORMATION: sulfide bond between Cys and Cys ( i i ) SEQUENCE DESCRIPTION: SEQ ID NO:13:

```
Cys  Lys  Lys  Lys  Lys  Lys  Cys
1                  5
```

(2) INFORMATION FOR SEQ ID NO:14:

(i) SEQUENCE CHARACTERISTICS:
        (A) LENGTH: 6 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:14:

Cys  Lys  Phe  Lys  Lys  Cys
     1                    5

(2) INFORMATION FOR SEQ ID NO:15:

(i) SEQUENCE CHARACTERISTICS:
        (A) LENGTH: 10 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:15:

Lys  Phe  Lys  Cys  Lys  Phe  Lys  Phe  Lys  Cys
 1              5                         10

(2) INFORMATION FOR SEQ ID NO:16:

(i) SEQUENCE CHARACTERISTICS:
        (A) LENGTH: 10 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:16:

Lys  Leu  Lys  Cys  Lys  Leu  Lys  Leu  Lys  Cys
 1              5                         10

(2) INFORMATION FOR SEQ ID NO:17:

(i) SEQUENCE CHARACTERISTICS:
        (A) LENGTH: 10 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:17:

Arg  Thr  Arg  Cys  Arg  Phe  Lys  Arg  Arg  Cys
 1              5                         10

(2) INFORMATION FOR SEQ ID NO:18:

(i) SEQUENCE CHARACTERISTICS:
        (A) LENGTH: 10 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:18:

Lys  Cys  Lys  Phe  Lys  Lys  Phe  Lys  Cys  Lys (2) INFORMATION FOR SEQ ID NO:19:

(i) SEQUENCE CHARACTERISTICS:
        (A) LENGTH: 10 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:19:

```
Cys  Lys  Lys  Lys  Lys  Phe  Phe  Phe  Phe  Cys
 1              5                         10
```

(2) INFORMATION FOR SEQ ID NO:20:

(i) SEQUENCE CHARACTERISTICS:
        (A) LENGTH: 12 amino acids
        (B) TYPE: amino acid
        (C) TOPOLOGY: circular (ix) FEATURE:
        (D) OTHER INFORMATION: sulfide bond between Cys and Cys (ii) SEQUENCE DESCRIPTION: SEQ ID NO:20:

```
Cys  Lys  Phe  Leu  Lys  Phe  Leu  Lys  Phe  Leu  Lys  Cys
 1              5                         10
```

(2) INFORMATION FOR SEQ ID NO:21:

(i) SEQUENCE CHARACTERISTICS:
        (A) LENGTH: 9 amino acids
        (B) TYPE: amino acid
        (C) TOPOLOGY: linear (ii) SEQUENCE DESCRIPTION: SEQ ID NO:21:

```
Val  Lys  Ala  Leu  Arg  Val  Arg  Arg  Leu
 1              5
```

(2) INFORMATION FOR SEQ ID NO:22:

(i) SEQUENCE CHARACTERISTICS:
        (A) LENGTH: 11 amino acids
        (B) TYPE: amino acid
        (C) TOPOLOGY: linear (ii) SEQUENCE DESCRIPTION: SEQ ID NO:22:

```
Lys  Ser  Leu  Ser  Leu  Lys  Arg  Leu  Thr  Tyr  Arg
 1              5                         10
```

(2) INFORMATION FOR SEQ ID NO:23:

(i) SEQUENCE CHARACTERISTICS:
        (A) LENGTH: 9 amino acids
        (B) TYPE: amino acid
        (C) TOPOLOGY: linear (ii) SEQUENCE DESCRIPTION: SEQ ID NO:23:

```
Lys  Val  Arg  Lys  Ser  Phe  Phe  Lys  Leu
 1              5
```

(2) INFORMATION FOR SEQ ID NO:24:

(i) SEQUENCE CHARACTERISTICS:
        (A) LENGTH: 9 amino acids
        (B) TYPE: amino acid
        (C) TOPOLOGY: linear ( i i ) SEQUENCE DESCRIPTION: SEQ ID NO:24:

Phe  Leu  Lys  Pro  Gly  Lys  Val  Lys  Val
       1                       5

( 2 ) INFORMATION FOR SEQ ID NO:25:

( i ) SEQUENCE CHARACTERISTICS:
      ( A ) LENGTH: 8 amino acids
      ( B ) TYPE: amino acid
      ( C ) TOPOLOGY: linear ( i i ) SEQUENCE DESCRIPTION: SEQ ID NO:25:

Lys  Glu  Leu  Lys  Arg  Ile  Lys  Ile
       1                       5

( 2 ) INFORMATION FOR SEQ ID NO:26:

( i ) SEQUENCE CHARACTERISTICS:
      ( A ) LENGTH: 9 amino acids
      ( B ) TYPE: amino acid
      ( C ) TOPOLOGY: linear ( i i ) SEQUENCE DESCRIPTION: SEQ ID NO:26:

Lys  Trp  Lys  Ala  Gln  Lys  Arg  Phe  Leu
       1                       5

( 2 ) INFORMATION FOR SEQ ID NO:27:

( i ) SEQUENCE CHARACTERISTICS:
      ( A ) LENGTH: 10 amino acids
      ( B ) TYPE: amino acid
      ( C ) TOPOLOGY: linear ( i i ) SEQUENCE DESCRIPTION: SEQ ID NO:27:

Lys  Trp  Lys  Ala  Gln  Lys  Arg  Phe  Leu  Lys
       1                       5                       10

( 2 ) INFORMATION FOR SEQ ID NO:28:

( i ) SEQUENCE CHARACTERISTICS:
      ( A ) LENGTH: 11 amino acids
      ( B ) TYPE: amino acid
      ( C ) TOPOLOGY: linear ( i i ) SEQUENCE DESCRIPTION: SEQ ID NO:28:

Lys  Arg  Leu  Lys  Trp  Lys  Tyr  Lys  Gly  Lys  Phe
       1                       5                       10

( 2 ) INFORMATION FOR SEQ ID NO:29:

( i ) SEQUENCE CHARACTERISTICS:
      ( A ) LENGTH: 13 amino acids
      ( B ) TYPE: amino acid
      ( C ) TOPOLOGY: circular ( i x ) FEATURE:
      ( D ) OTHER INFORMATION: sulfide bond between Cys and Cys ( i i ) SEQUENCE DESCRIPTION: SEQ ID NO:29:

Cys  Gln  Ser  Trp  Lys  Ser  Ser  Glu  Ile  Arg  Cys  Gly  Lys
       1                       5                       10

( 2 ) INFORMATION FOR SEQ ID NO:30:

( i ) SEQUENCE CHARACTERISTICS:
      ( A ) LENGTH: 6 amino acids
      ( B ) TYPE: amino acid ( C ) TOPOLOGY: circular ( i i ) SEQUENCE DESCRIPTION: SEQ ID NO:30:

Lys   Phe   Leu   Lys   Lys   Thr
      1                            5

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( C ) TOPOLOGY: circular ( i i ) SEQUENCE DESCRIPTION: SEQ ID NO:31:

Glu   Tyr   Val   Glu   Tyr   Val   Glu   Tyr   Val
      1                            5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) TOPOLOGY: circular ( i x ) FEATURE:
        ( D ) OTHER INFORMATION: sulfide bond between Cys and Cys ( i i ) SEQUENCE DESCRIPTION: SEQ ID NO:32:

Cys   Lys   Phe   Leu   Lys   Cys
      1                            5

( 2 ) INFORMATION FOR SEQ ID NO:33:

( i ) SEQUENCE CHARACTERISTICS:
        ( A ) LENGTH: 8 amino acids
        ( B ) TYPE: amino acid
        ( C ) TOPOLOGY: circular ( i i ) SEQUENCE DESCRIPTION: SEQ ID NO:33:

Ile   Gln   Leu   Pro   His   Lys   Lys   Ile
      1                            5

( 2 ) INFORMATION FOR SEQ ID NO:34:

( i ) SEQUENCE CHARACTERISTICS:
        ( A ) LENGTH: 9 amino acids
        ( B ) TYPE: amino acid
        ( C ) TOPOLOGY: circular ( i i ) SEQUENCE DESCRIPTION: SEQ ID NO:34:

His   Tyr   Arg   Ile   Asn   Pro   Thr   Val   Lys
      1                            5

( 2 ) INFORMATION FOR SEQ ID NO:35:

( i ) SEQUENCE CHARACTERISTICS:
        ( A ) LENGTH: 13 amino acids
        ( B ) TYPE: amino acid
        ( C ) TOPOLOGY: circular ( i x ) FEATURE:
        ( D ) OTHER INFORMATION: sulfide bond between Cys and Cys ( i i ) SEQUENCE DESCRIPTION: SEQ ID NO:35:

Cys   Arg   Gln   His   Gly   Thr   Tyr   Ile   Asn   Cys   Leu   His   Val
      1                            5                         10

PEPTIDES FOR NEUTRALIZING THE TOXICITY OF LIPID A

This application is a continuation-in-part of Ser. No. 08/049,871, filed Apr. 19, 1993, which is now U.S. Pat. No. 5,358,933 and Ser. No. 07/819,893, filed Jan. 16, 1992, which is now U.S. Pat. No. 5,371,186. Ser. No. 08/049,871, filed Apr. 19, 1993, which is now U.S. Pat. No. 5,358,933 is a continuation of Ser. No. 07/658,744 filed Feb. 11, 1991, now abandoned. Ser. No. 07/819,893, filed Jan. 16, 1992, which is now U.S. Pat. No. 5,371,186 is a continuation-in-part of Ser. No. 07/658,744, filed Feb. 11, 1991, now abandoned.

FIELD OF THE INVENTION

The present invention is concerned with providing peptides that are useful as therapeutic and/or prophylactic agents because of their ability to bind and neutralize the toxic activity of endotoxin.

BACKGROUND OF THE INVENTION

Septic shock is a well defined clinical syndrome that is caused by the release of endotoxin or lipopolysaccharide (LPS) by gram negative bacteria. It is known that the endotoxin which is the major antigen which is present in the outer membrane of gram-negative bacteria, is a glycophospholipid which is extremely toxic to mammalian hosts by virtue of its ability to bind, via its toxic moiety Lipid A, on target cells of the immune system such as macrophage and monocytes. The binding results in the massive release of cytokines such as Tumor Necrosis Factor (TNF), Interleukin 1 and 6 (IL-1 and IL-6) as well as gamma Interferon (IFN-gamma), which are the central mediators of LPS-induced shock which can be lethal to the host. The mortality rate in humans due to LPS-induced shock as a consequence of bacterial sepsis, has been estimated in 30–50% of the cases with documented sepsis within 24–48 hours from the onset of the symptoms of the infection. It is also known that endotoxin is a harmful contaminant that has been detected in biologicals and other preparations for parenteral use in humans and animals.

It is known that cationic molecules such as the homologous polymers of basic amino acids, such as, Lysine, have the ability to interact with cell membranes that contain anionic phospholipids. As a result of the interaction between cationic structures and glycophospholipids, one may speculate that homologous polymers of basic (cationic) amino acids might serve as agents to bind and detoxify bacterial LPS. These linear homopolymers of the basic amino acids have the capability of promoting cell to cell fusion and can cause a disruption of the cell membrane of the interacting cells which leads to cell death.

The applicant has discovered that certain peptides which contain the basic amino acid units (homopolymer units) as well as the basic and hydrophobic amino acids (heteropolymer units) according to the formulae: $(A)_n$, $(AB)_n$, and $(ABC)_n$ where A is any aliphatic cationic amino acid (at a pH of about 7.0); B and C are any hydrophobic amino acid, both (the aliphatic cationic amino acid and the hydrophobic amino acid) that are characterized by solvent parameter values equal to or greater than +1.5 kcal/mol and −1.5 kcal/mol respectively, will bind to the Lipid A moiety of LPS and will detoxify Lipid A in vitro and in vivo and thus neutralize the effects of endotoxin. The minimal effective peptide sequence to bind Lipid A has been found to be six to seven amino acid residues containing a minimum of three aliphatic cationic amino acids, with a ratio of aliphatic cationic amino acids to hydrophobic amino acids of equal to or greater than 0.5 ($R_{c/h}$, wherein c is the number of cationic amino acids in the peptide and h is the number of hydrophobic amino acids in the peptide). This ratio is the minimum required for binding Lipid A although high affinity binding of the peptide to Lipid A is reached with sequences of ten amino acids with a ratio ($R_{c/h}$) equal to or greater than 1.0.

Accordingly, it is a primary object of the invention to identify peptides that will bind Lipid A.

It is also an object of the invention to provide novel compositions for the treatment or prevention of septic shock which are based on the peptides which have been identified as a class of peptides that are useful in the present invention.

It is also an object of the invention to provide novel methods for the treatment or prevention of septic shock which are based on the use of the peptides which have been identified as a class of peptides that are useful according to the present invention.

It is also an object of this invention to provide novel compositions and methods for the detoxification of biologicals.

These and other objects of the invention will become apparent from the appended specification.

SUMMARY OF THE INVENTION

The present invention provides a novel method for binding endotoxin using linear or cyclic peptides having units of the formula:

(a) $(A)_n$ wherein A is Lysine or Arginine and n is an integer with a minimum value of 7;

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2.

The preferred peptides for use in the invention will also have a ratio of aliphatic cationic amino acids to hydrophobic amino acids ($R_{c/h}$) of at least 0.5 and within the range of about 0.5 to 10.0 which is computed by using the solvent parameter values only for those amino acids which are present in the peptides which have a solvent parameter value equal to or greater than +1.5 kcal/mol (lysine and arginine) and −1.5 kcal/mol (valine, isoleucine, leucine, tyrosine, phenylalanine and tryptophane) as measured according to Levitt, J. Mol. Biol. 104,59 (1976), which is incorporated by reference.

The peptide units which are represented by formula (a), (b) and (c) represent discrete peptides which will bind endotoxin as estimated by the LAL inhibition test and have specific formulas which are identical with the units of formula (a), (b) and (c) as well as peptides which will bind endotoxin in the LAL inhibition test and which include as a part of their structure units of formula (a), (b) and (c), in addition to other amino acids, are included within the peptides which comprise the invention. For in vivo use, the preferred peptides should not exhibit hemolytic activity when equal volumes of a solution of the peptide in isotonic saline, at a minimum peptide concentration of 0.1 mg/ml and a solution of 10% w/w fresh human erythrocytes in isotonic saline are incubated at 37° C. for 30 minutes and no rupture of the erythrocytes and release of hemoglobin is detected visually or by use of a spectrophotometer (540 nm).

The minimum values for n, m and p have been determined experimentally on the basis of the observation that when the peptide is linear, it will have at least 7 amino acid units and when said peptide is cyclic or a polymer having several cycles, i.e. 2 to 6 cycles, it will have a ring structure that has a minimum of 6 amino acid units and a maximum of 7 amino acid units; said peptides having a ratio of aliphatic cationic amino acids to hydrophobic amino acids which is equal to or greater than 0.5.

When the peptides are of the formula $(A)_n$, $(AB)_m$ or $(ABC)_p$, i.e. when these formulas do not represent units of a larger peptides, n will be from 7 to 500; m will be from 3 to 200 and p will be from 2 to 100.

The peptides of formula $(A)_n$ when n is from 7 to 10 are novel peptides and the peptides of formulas $(AB)_m$ and $(ABC)_p$ are novel Peptides. The invention also includes novel Pharmaceutical compositions which are based on the disclosed peptides and methods for treating or preventing septic shock which are based on the use of the peptides described herein which show no substantial hemolytic activity according to the procedure for testing for hemolytic activity which is set forth above.

DETAILED DESCRIPTION OF THE INVENTION

The applicant has discovered what is being characterized as the minimal peptide structure which will bind endotoxin. These structures are comprehended by peptides having units of the formulas:

(a) $(A)_n$ wherein A and n are as defined above;

(b) $(AB)_m$ wherein A, B and m are as defined above; and (c) $(ABC)_p$ wherein A, B, C and D are as defined above.

These peptides include novel synthetic peptides and peptides which are known. Examples of the peptides are listed below. Those peptides which are not novel are marked by an asterisk:

$(Lys)_{10}$ (SEQ ID NO: 1);
$(Lys)_{30}$* (SEQ ID NO: 2);
$(Lys)_{434}$* (SEQ ID NO: 3);
$(Lys-Glu)_5$ (SEQ ID NO: 4);
$(Lys-Phe)_5$ (SEQ ID NO: 5);
Lys—Phe—Leu—Lys—Lys—Thr—Leu (SEQ ID NO: 6);
$(Lys-Phe-Leu)_2-Lys$ (SEQ ID NO: 7);
$(Lys-Phe-Leu)_3-Lys$ (SEQ ID NO: 8);
$(Arg-Tyr-Val)_3$ (SEQ ID NO: 9);
$(Lys-Phe-Phe)_3-Lys$ (Seq ID NO: 10);
$(Lys-Leu-Leu)_3$ (SEQ ID NO: 11);
$(Lys)_6(Phe-Lys)_2$ (SEQ ID NO: 12);

Cys—(Lys)₅—Cys
s------------s (SEQ ID NO: 13);

Cys—Lys—Phe—Lys—Lys—Cys
s---------------------s (SEQ ID NO: 14);

Lys—Phe—Lys—Cys—Lys—Phe—Lys—Phe—Lys—Cys
                          s---------------------------s (SEQ ID NO: 15);

Lys—Leu—Lys—Cys—Lys—Leu—Lys—Cys
                     s------------------s (SEQ ID NO: 16);

Arg—Thr—Arg—Cys—Arg—Phe—Lys—Arg—Arg—Cys
                          s---------------------------s (SEQ ID NO: 17);

Lys—Cys—(Lys—Phe—Lys)₂—Cys—Leu
      s---------------------s (SEQ ID NO: 18);

Cys—(Lys)₄—(Phe)₄—Cys
s--------------------s (SEQ ID NO: 19);

Cys—(Lys—Phe—Leu)₃—Lys—Cys
s--------------------------s (SEQ ID NO: 20);

Val—Lys—Ala—Leu—Arg—Val—Arg—Arg—Leu (SEQ ID NO: 21);
Lys—Ser—Leu—Ser—Leu—Lys—Arg—Leu—Thr—Tyr—Arg (SEQ ID NO: 22);
Lys—Val—Arg—Lys—Ser—Phe—Phe—Lys—Leu (SEQ ID NO: 23);
Phe—Leu—Lys—Pro—Gly—Lys—Val—Lys—Val (SEQ ID NO: 24);
Lys—Glu—Leu—Lys—Arg—Ile—Lys—Ile (SEQ ID NO: 25);
Lys—Trp—Lys—Ala—Gln—Lys—Arg—Phe—Leu (SEQ ID NO: 26);
Lys—Trp—Lys—Ala—Gln—Lys—Arg—Phe—Leu—Lys (SEQ ID NO: 27);
Lys—Arg—Leu—Lys—Trp—Lys—Tyr—Lys—Gly—Lys—Phe (SEQ ID NO: 28); and Cys—Gln—Ser—Trp—Lys—Ser—Ser—Glu—Ile—Arg—Cys—Gly—Lys
s---------------------------------s (SEQ ID NO: 29).

The peptides for use in the present invention may be synthesized by classical methods of peptide chemistry using manual or automated techniques as well as by DNA recombinant technology. The synthetic procedure comprises solid phase synthesis by Fmoc chemistry, cleavage (TFA 95%+ Et-(SH)₂ 5%), followed by vacuum evaporation. Thereafter, the product is dissolved in 10% acetic acid, extracted with ether, concentrated at 0.1 mg/ml at pH of 6.0–7.5. Stirring under filtered air followed for 1 to 6 hours in case of the Cysteine-containing peptides and finally desalting by reverse phase chromatography is carried out.

A particular automated method of preparing peptides for use in the present invention is based on the use of an automatic synthesizer (Milligen Mod.9050 (MILLIPORE, Burlington, Mass.) on a solid phase support of polyamide/ Kieselguhr resin (2.0 g). The amino acids used in the synthesis of the peptide analogs are Fmoc-aa-Opfp derivatives (9-Fluorenylmethyloxycarbonyl-aa-O-pentafluorophenyl ester) of each amino acid(aa) involved in the considered sequences using 0.8 mol of each amino acid to sequentially form the peptide.

Each cycle of synthesis may be performed at room temperature (20° C.) and involves the following steps of reaction:

Step 1—Deprotection

The first aa Fmoc-protected at the amino group, was treated with a 20% solution of piperidine for 7 minutes in order to remove the Fmoc alpha-protecting group. Washing with dimethylformamide followed for 12 minutes to remove all traces of piperidine. Deprotection and washing were run continuously through the column containing the resin by means of a pump at a flow of 5 ml/min.

Step 2—Activation of the Fmoc-aa-Opfp derivative

The amino and carboxy-protected aminmo acid due, according to the desired sequence, was activated after its dissolution in 5 ml of dimethylformamide, by a catalytic amount of hydroxybenzotriazol (0.5 ml of a 5% w/v solution in dimethylformamide).

Step 3—Acylation

The activated and protected Fmoc-aa-Opfp derivative was then recycled for 30 minutes through the column by the pump at 5 ml/min in order to obtain coupling of the introduced aa at the alpha-amino group (previously deprotected as reported in Step 1) of the amino acid preceding the new one in the desired sequence.

Step 4—Washing

Washing of the matrix in the column followed by dimethylformamide for 2 minutes at 5 ml/min before a new cycle began.

At the completion of the synthesis, the peptide on the resin support was cleaved by 95% Trifluoroacetic acid (TFA) with 5% Ethane dithiol as a scavenger, if Cysteine residues were present in the aa sequence, at room temperature for 2 hours. After separation of the cleaved peptide from the resin by filtration, the solution was concentrated by vacuum evaporation to dryness. The collected solid residue was then solubilized in 10% acetic acid at a concentration of 10–20 mg/ml and several extractions by diethyl ether followed (six to eight extractions with half the volume of the peptide solution) in order to remove the scavenger Ethane dithiol. The peptide solution was then neutralized by 0.1N ammonium hydroxide and adjusted to the concentration of roughly 0.1 mg/ml. The solution was then stirred under air for 1 to 6 hours in order to obtain the selective oxidation of the two sulfhydryl groups belonging to the Cys residues of the sequence. In this way, only monomeric oxidized peptides were obtained with no traces of polymeric material. The solution of oxidized peptide was then desalted by reverse-phase chromatography on SEP-PAK C-18 cartridges (MILLIPORE) and finally freeze dried. The products were analyzed by high-performance liquid chromatography (HPLC) analysis as well as by chemical analysis of the synthetic structures.

Fast atom bombardment was used to confirm the calculated mass of the peptides. The polymeric peptide of the formula $(A)_n$ when n was 10 was prepared by solid phase FMOC synthesis.

The peptides described herein which exhibit the absence or a low level of hemolysis may be used in the treatment of septic shock in mammals including humans at doses of about 0.1 µg–2.0 mg/kg of body weight or may be used at a level of about 10 µg to about 0.1 mg/kg of body weight and the amount may be administered in divided doses on daily basis. The peptides may be administered prophylactically to patients who may be exposed to or have been exposed to organisms which may cause septic shock or to detoxify bacterial endotoxins by the use of the same dose set forth above in vivo. In vitro detoxification or prevention of endotoxin contamination may be carried out at a level which is effective to achieve the desired result. The amount may be based on routine experimentation based on the premise that 1 mole of Lipid A endotoxin is bound by 1 mole of peptide. The particular dose of a particular peptide may be varied within or without the range that is specified herein depending on the particular application or severity of a disease and the condition of the host. Those who are skilled in the art may ascertain the proper dose using standard procedures.

The compounds may be administered intravenously and parenterally using well known pharmaceutical carriers or inert diluents. Oral administration is not preferred because the peptides will tend to be degraded by the enzymes of the alimentary tract. Water or isotonic saline are preferred diluents and a concentration of 0.1 mg per ml may be used. Preferably, the compounds will be stored in a dry form and will be dissolved in the diluent immediately prior to administration.

Generally, for the production of a vaccine against endotoxin, complexes of Lipid-A and LPS with the peptides of the invention may be made using stoichiometric amounts of Lipid-A or LPS with the peptide. The amounts of complex also able to induce antibody in a host are not critical; about 1 mcg of Lipid-A in the complex with the peptide will be effective in safely inducing antibodies in a host.

The detoxification activity of the peptides has been confirmed in vitro by the inhibition of the LPS-activated enzymatic cascade leading to clot formation in Limulus Amebocyte Lysate (LAL) assay which is described in Science, 259, pp361–365 (1993), which is incorporated by reference. Detoxification activity in vivo has been confirmed by inhibition of the Lipid A-mediated hemorragic dermonecrosis in the rabbit. Inhibition in the LAL assay is a very sensitive method of detecting even small differences in LPS activity (LPS detection level=10 pg/ml) and correlates with the inhibition of cytokine-mediated pyrogenicity in the rabbit. This test has been accepted by the U.S. Food and Drug Administration as an end product endotoxin test for human and animal parenteral drugs. Skin hemorraghic necrosis in the rabbit, which was first described by G. Schwartzman as a local reaction to LPS toxicity (Proc. Soc. Exp. Biol. Med., 25:560, 1928) was chosen because Lipid A is responsible for this inflammatory process in the derma (an area where cells rich in LPS-specific CD14-receptor proteins like leukocytes and macrophages predominate) through induction of the release of TNF and IFN-gamma. These factors are the central mediatiors of LPS induced shock in sepsis caused by Gram-negative bacteria. The inhibition of LPS-induced cytokines (TNF, Interleukin-1, Interleukin-6 and the like) result in a significant increase in the survival rate in animal models that are challenged by a lethal dose of LPS.

The invention also includes the use of the peptides to contact systems containing endotoxin dispersed in a fluid for the purpose of detoxifying the endotoxin. This procedure may be used to detoxify biopharmaceuticals such as vaccines, solutions of drugs, injectable nutrient solutions, and the like. The invention further comprises the use of the peptides as additives for fluids which will support bacterial growth that will produce endotoxin. The presence of the non-toxic peptide will detoxify any endotoxin which is subsequently elaborated.

DESCRIPTION OF THE PREFERRED EMBODIMENTS

Example 1

Table 1 contain the results of the testing of novel amino acid sequences of the invention. These peptides include linear cationic homopolymeric peptides of various sizes which have high affinity for the Lipid A moiety of endotoxin and result in the detoxification of endotoxin. However, certain linear cationic homopolymeric peptides show a strong hemolytic activity on human erythrocytes. Their stability to proteolysis in human serum or whole blood is also important for in vivo use. Those peptides that exhibit high levels of hemolytic activity (above 1.5 mg/ml) are not useful in vivo for binding endotoxin but are useful in vitro for the detoxification of biologicals by causing the peptides to bind endotoxin in the biological and form a complex which can be removed by conventional techniques such as by filtration with a suitable ultrafilter such as an anisotropic filter having an average pore size of 0.01 µm or can be separated as a complex on solid phase matrixes.

TABLE 1

| Peptides | $R_{c/h}$* | $K_a$ ($\times 10^7$ M$^{-1}$) | LAL Inh. (w/w) | t/2** (min) | Hemolysis*** (mg/Ml) |
|---|---|---|---|---|---|
| (Lys)$_{10}$ (SEQ ID NO: 1) | | 1.20 | 1 | 5 | >1.50 |
| (Lys)$_{30}$ (SEQ ID NO: 2) | | 1.35 | 1 | 30 | 0.17 |
| (Lys)$_{434}$ (SEQ ID NO: 3) | | 1.38 | 1 | 45 | 0.07 |
| (Lys—Glu)$_5$ (SEQ ID NO: 4) | | 0.23 | 1 | 60 | >1.50 |
| (Lys—Phe)$_5$ (SEQ ID NO: 5) | 1.00 | 1.57 | 1 | 2 | 0.02 |
| (Lys—Phe—Leu—Lys—Lys—Thr—Leu (SEQ ID NO: 6) | 1.00 | 0.16 | 100 | N.D. | N.D. |
| (Lys—Phe—Leu)$_2$—Lys (SEQ ID NO: 7) | 0.75 | 0.10 | 100 | 7 | >1.50 |
| (Lys—Phe—Leu)$_3$—Lys (SEQ ID NO: 8) | 0.67 | 1.17 | 2 | 4 | 0.03 |
| (Arg—Tyr—Val)$_3$ (SEQ ID NO: 9) | 0.50 | 0.26 | 100 | 35 | 1.00 |
| (Lys—Phe—Phe)$_3$ —Lys (Seq ID NO: 10) | 0.67 | 0.33 | 1 | 120 | 0.04 |
| (Lys—Leu—Leu)$_3$ (SEQ ID NO: 11) | 0.50 | 0.16 | 1 | 110 | 0.11 |
| (Lys)$_6$(Phe—Lys)$_2$ (SEQ ID NO: 12) | 1.50 | 0.92 | 1 | 2 | 0.02 |
| Cys—(Lys)$_5$—Cys<br>s----------s (SEQ ID NO: 13) | | 0.19 | 1 | 15 | >1.50 |
| Cys—Lys—Phe—Lys—Lys—Cys<br>s--------------------s (SEQ ID NO: 14) | 3.00 | 0.02 | 10 | 50 | >1.50 |
| Lys—Phe—Lys—Cys—Lys—Phe—Lys—Phe—Lys—Cys<br>s--------------------------s (SEQ ID NO: 15) | 1.67 | 0.25 | 1 | 60 | >1.50 |
| Lys—Leu—Lys—Cys—Lys—Leu—Lys—Leu—Lys—Cys<br>s--------------------------s (SEQ ID NO: 16) | 1.67 | 0.90 | 1 | 100 | >1.50 |
| Arg—Thr—Arg—Cys—Arg—Phe—Lys—Arg—Arg—Cys<br>s----------------------------s (SEQ ID NO: 17) | 2.50 | 1.05 | 1 | 75 | 1.00 |
| Lys—Cys—(Lys—Phe—Lys)$_2$—Cys—Lys<br>s--------------------s (SEQ ID NO: 18) | 1.00 | 1.05 | 1 | 60 | 0.10 |
| Cys—(Lys)$_4$—(Phe)$_4$—Cys<br>s-----------------s (SEQ ID NO: 19) | 1.00 | 1.10 | 1 | 210 | 0.37 |
| Cys—(Lys—Phe—Leu)$_3$—Lys—Cys<br>s----------------------s (SEQ ID NO: 20) | 0.67 | 1.05 | 1 | 90 | 0.001 |
| Lys—Phe—Leu—Lys—Lys—Thr* SEQ ID NO: 30 | 1.50 | 0 | 0 | N.D. | N.D. |
| (Glu—Tyr—Val)$_3$* SEQ ID NO: 31 | 0.00 | 0 | 0 | N.D. | N.D. |
| Cys—Lys—Phe—Leu—Lys—Cys*<br>s---------------------s  SEQ ID NO: 32 | 1.00 | 0 | 0 | N.D. | >1.50 |

*control

Rc/h defines the ratio between aliphatic cationic and hydrophobic amino acids present in a given sequence. Only amino acids with solvent parameter values assigned by Levitt (J. Mol. Biol. 104,59(1976) equal to or greater than +1.5 kcal/mol (lysine and arginine) and −1.5 kcal/mol (valine, isoleucine, leucine, tyrosine, phenylalanine and trystophane) were considered for calculating the ratios.

Example 2

This example shows the activity of primary amino acid sequences which occur in natural proteins. These sequences specifically bind endotoxins of heterologous Gram-negative bacteria. In the footnote to Table II, the proteins where the sequences of the peptides occur naturally are identified. Each of the peptides of Table II were prepared synthetically using the procedures that have been set forth above. The data in Table II shows the activity of the peptides:

TABLE II

| | Peptides | $R_{c/h}$* | Ka ($\times 10^7$ M$^{-1}$) | LAL Inh. (w/w) | t/2** (min) | Hemolysis*** (mg/Ml) |
|---|---|---|---|---|---|---|
| 1. | Val—Lys—Ala—Leu—Arg—Val—Arg—Arg—Leu (SEQ ID NO: 21) | 100 | 0.02 | 100 | 35 | >1.50 |
| 2. | Lys—Ser—Leu—Ser—Leu—Lys—Arg—Leu—Thr—Tyr—Arg (SEQ ID NO: 22) | 100 | 0.04 | 200 | 100 | >1.50 |
| 3. | Lys—Val—Arg—Lys—Ser—Phe—Phe—Lys—Leu (SEQ ID NO: 23) | 1.00 | 0.08 | 100 | 60 | 0.50 |
| 4. | Phe—Leu—Lys—Pro—Gly—Lys—Val—Lys—Val (SEQ ID NO: 24) | 0.60 | 0.05 | 100 | 105 | >1.50 |
| 5. | Lys—Glu—Leu—Lys—Arg—Ile—Lys—Ile SeqID NO: 25) | 1.33 | 0.05 | 100 | 70 | >1.50 |
| 6. | Lys—Trp—Lys—Ala—Gln—Lys—Arg—Phe—Leu (SEQ ID NO: 26) | 1.33 | 0.03 | 100 | 50 | >1.50 |
| 7. | Lys—Trp—Lys—Ala—Gln—Lys—Arg—Phe—Leu—Lys (SEQ ID NO: 27) | 1.67 | 0.23 | 10 | 40 | >1.50 |
| 8. | Lys—Arg—Leu—Lys—Trp—Lys—Tyr—Lys—Gly—Lys—Phe (SEQ ID NO: 28) | 1.50 | 1.83 | 1 | 55 | 0.50 |
| 9. | Cys—Gln—Ser—Trp—Lys—Ser—Ser—Glu—Ile—Arg—Cys—Gly—Lys<br>s----------------------------------s (SEQ ID NO: 29) | 1.50 | 2.10 | 1 | 55 | 0.50 |
| a. | Ile—Gln—Leu—Pro—His—Lys—Lys—Ile* SEQ ID NO: 33 | 0.67 | 0 | >1000 | N.D. | N.D. |
| b. | His—Tyr—Arg—Ile—Asn—Pro—Thr—Val—Lys* SEQ ID NO: 34 | 0.67 | 0 | >1000 | N.D. | N.D. |
| c. | Cys—Arg—Gln—His—Gly—Thr—Tyr—Ile—Asn—Cys—Leu—His—Val*<br>s------------------------------------s SEQ ID NO: 35 | 0.25 | 0 | >1000 | N.D. | N.D. |

*Control
1. CD14 67–75 Human E. Ferrero and S. M. Goyert, Nucl. Acid Res. 16,4173 (1988)
2. CD14 68–78 Mouse E. Ferrero and S. M. Goyert, Nucl. Acid Res. 16,4173 (1988)
3. LBP 92–100 R. R. Schumann et al. Science, 249,1429 (1990); S.D. Wright et al. ibid, 249, 1431 (1990)
4. LBP 376–384 Human R. R. Schumann et al. Science, 249,1429 (1990); S.D. Wright et al. ibid, 249, 1431 (1990)
5. BPI 27–34 Humane C. E. Ooi, J. Weiss, M. E. Doerfler, OP. Elsbach, J. Exp. Med. 174,649 (1991)
6. BPI 90–98 Human C. E. Ooi, J. Weiss, M. E. Doerfler, OP. Elsbach, J. Exp. Med. 174,649 (1991)
7. BPI 90–99 Human C. E. Ooi, J. Weiss, M. E. Doerfler, OP. Elsbach, J. Exp. Med. 174,649 (1991)
8. LALF 41–51 J. Aketagawa et al., J. Biol. Chem,261,7357 (1986)
9: LEBP-PI 5–17 Crab C. A. S. A. Minetti, Y. Lin, T. Cislo. T. Y. Liu, J. Biol. Chem, 266, 20773 (1991)
a. BPI 153–160 Human
b. Lalf 33–41 Crab
c. LEBP-PI 86–98 Crab

---

I claim:

1. A peptide consisting of the formula: (Lys-Phe)$_5$ (SEQ ID NO: 5).

2. A peptide consisting of the formula: Lys-Phe-Leu-Lys-Lys-Thr-Leu (SEQ ID NO: 6).

3. A peptide consisting of the formula: (Lys-Phe-Phe)$_3$-Lys (SEQ ID NO: 10).

4. A peptide consisting of the formula:

(Lys-Leu-Leu)$_3$ (SEQ ID NO: 11).

5. A peptide consisting of the formula:

(Lys)$_6$(Phe-Lys)$_2$ (SEQ ID NO: 12).

6. A peptide consisting of the formula:

Cys—(Lys)$_5$—Cys
s----------- s  (SEQ ID NO: 13).

7. A peptide consisting of the formula:

Cys—Lys—Phe—Lys—Lys—Cys
s---------------------- s (SEQ ID NO: 14).

8. A peptide consisting of the formula:

Lys—Phe—Lys—Cys—Lys—Phe—Lys—Phe—Lys—Cys
           s---------------------------- s
(SEQ ID NO: 15).

9. A peptide consisting of the formula:

Lys—Leu—Lys—Cys—Lys—Leu—Lys—Leu—Lys—Cys
           s---------------------------- s
(SEQ ID NO: 16).

10. A peptide consisting of the formula:

Arg—Thr—Arg—Cys—Arg—Phe—Lys—Arg—Arg—Cys
           s---------------------------- s
(SEQ ID NO: 17).

11. A peptide consisting of the formula:

Lys—Cys—(Lys—Phe—Lys)$_2$—Cys—Lys
     s--------------------- s  (SEQ ID NO: 18).

12. A peptide consisting of the formula:

Cys—(Lys)$_4$—(Phe)$_4$—Cys
s------------------ s (SEQ ID NO: 19).

13. A peptide consisting of the formula:

Lys-Ser-Leu-Ser-Leu-Lys-Arg-Leu-Thr-Tyr-Arg (SEQ ID NO:22).

14. A peptide consisting of the formula: Lys-Val-Arg-Lys-Ser-Phe-Phe-Lys-Leu (SEQ ID NO: 23).

15. A peptide consisting of the formula: Phe-Leu-Lys-Pro-Gly-Lys-Val-Lys-Val (SEQ ID NO: 24).

16. A peptide consisting of the formula: Lys-Glu-Leu-Lys-Arg-Ile-Lys-Ile (SEQ ID NO: 25).

17. A peptide consisting of the formula:

Cys—Gln—Ser—Trp—Lys—Ser—Ser—Glu—Ile—Arg—Cys—Gly—Lys
s----------------------------------------- s   (SEQ ID NO: 29).

18. A peptide composition which includes a pharmaceutical carrier and a peptide of claim 1.

19. A peptide composition which includes a pharmaceutical carrier and a peptide of claim 2.

20. A peptide composition which includes a pharmaceutical carrier and a peptide of claim 3.

21. A peptide composition which includes a pharmaceutical carrier and a peptide of claim 4.

22. A peptide composition which includes a pharmaceutical carrier and a peptide of claim 5.

23. A peptide composition which includes a pharmaceutical carrier and a peptide of claim 6.

24. A peptide composition which includes a pharmaceutical carrier and a peptide of claim 7.

25. A peptide composition which includes a pharmaceutical carrier and a peptide of claim 8.

26. A peptide composition which includes a pharmaceutical carrier and a peptide of claim 9.

27. A peptide composition which includes a pharmaceutical carrier and a peptide of claim 10.

28. A peptide composition which includes a pharmaceutical carrier and a peptide of claim 11.

29. A peptide composition which includes a pharmaceutical carrier and a peptide of claim 12.

30. A peptide composition which includes a pharmaceutical carrier and a peptide of claim 13.

31. A peptide composition which includes a pharmaceutical carrier and a peptide of claim 14.

32. A peptide composition which includes a pharmaceutical carrier and a peptide of claim 15.

33. A peptide composition which includes a pharmaceutical carrier and a peptide of claim 16.

34. A peptide composition which includes a pharmaceutical carrier and a peptide consisting of the formula:

Lys-Arg-Leu-Lys-Trp-Lys-Tyr-Lys-Gly-Lys-Phe (SEQ ID NO:28).

35. A peptide composition which includes a pharmaceutical carrier and a peptide of claim 17.

36. A peptide composition which comprises a peptide of the formula (Lys)$_{30}$ (SEQ ID NO: 2) and a pharmaceutical carrier.

37. A peptide composition which comprises a peptide of the formula (Lys)$_{434}$ (SEQ ID NO: 3) and a pharmaceutical carrier.

38. A method of treating or preventing septic shock which comprises administering to a mammal an effective amount of the peptide composition of claim 36.

39. A method of treating or preventing septic shock which comprises administering to a mammal an effective amount of the peptide composition of claim 37.

* * * * *